United States Patent
Didenko et al.

(10) Patent No.: US 6,864,058 B2
(45) Date of Patent: Mar. 8, 2005

(54) VACCINIA TOPOISOMERASES I-BASED ASSAYS FOR DETECTION OF SPECIFIC DNA BREAKS

(75) Inventors: Vladimir Didenko, Houston, TX (US); David Baskin, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 10/068,065

(22) Filed: Feb. 6, 2002

(65) Prior Publication Data

US 2004/0091859 A1 May 13, 2004

(51) Int. Cl.[7] ............................ C12Q 1/68; G01N 1/30; G01N 33/48; C07H 21/02; C07H 21/04
(52) U.S. Cl. ..................... 435/6; 435/40.5; 536/23.1; 536/24.3
(58) Field of Search ................. 435/6, 40.5; 536/23.1, 536/24.3

(56) References Cited

U.S. PATENT DOCUMENTS

| | | | | |
|---|---|---|---|---|
| 5,296,375 A | * | 3/1994 | Kricka et al. | |
| 5,304,487 A | * | 4/1994 | Wilding et al. | |
| 5,856,174 A | * | 1/1999 | Lipshutz et al. | |
| 5,904,824 A | * | 5/1999 | Oh | |
| 6,013,438 A | * | 1/2000 | Didenko et al. | |

FOREIGN PATENT DOCUMENTS

| | | |
|---|---|---|
| WO | IB-94/05414 A1 * | 3/1994 |
| WO | IB-98/23777 A2 * | 6/1998 |

OTHER PUBLICATIONS

Bantel, Heike, et al.; Detection of Elevated caspase activation and early apoptosis in liver diseases; European Journal of Cell Biology, vol.80, pp. 230–239, Mar. 2001.

Barry, Michael A., et al.; Identification of Deoxyribonuclease II as an Endonuclease Involved in Apoptosis; Archives of Biochemistry and Biophysics, vol. 300 (1), pp. 440–450, Jan., 1993.

Bernardi, Giorgio; Spleen Acid Deoxyribonuclease; In The Enzymes (ed Boyer, P.D.) v. 4, pp 271–287 (Academic Press, New York: 1971).

Byassee, Tyler A., et al.; Probing Single Molecules in Single Living Cells; Anal. Chem. 2000, 72, pp 5606–5611.

Darzynkiewicz, Z., et al.; Review Article—Features of Apoptotic Cells Measured by Flow Cytometry; Cytometry 13:795–808 (1992).

Didenko, Vladimir V., et al.; Presence of Double–strand Breaks with Single–base 3'Overhangs in Cells Undergoing Apoptosis by Not Necrosis; The Journal of Cell Biology, vol. 135 95), pp 1369–1376, Dec. 1996.

Didenko, Vladimir V., et al.; Benchmarks—Substantial Background Reduction in Ligase–Based Apoptosis Detection Using Newly Designed Hairpin Oligonucleotide Probes; Bio Techniques 27:1130–1132 (Dec. 1999).

Didenko, Vladimir V., et al.; Technical Advance—Biotin–Labeled Hairpin Oligonucleotides; American Journal of Pathology, vol. 152 (4), pp 897–902, Apr. 1998.

(List continued on next page.)

*Primary Examiner*—Jeffrey Fredman
*Assistant Examiner*—Teresa Strzelecka
(74) *Attorney, Agent, or Firm*—Fulbright & Jaworski, LLP

(57) ABSTRACT

Several types of DNA cuts are used as markers of apoptosis for detection of apoptotic cells in situ. The present invention includes a method to detect DNase II type DNA damage, bearing 5'OH using vaccinia topoisomerase I. The present invention also includes a method combining a ligase-based method to detect DNase I type DNA damage and the topoisomerase based method, resulting in simultaneous detection of two specific types of DNA damage in situ.

50 Claims, 3 Drawing Sheets

OTHER PUBLICATIONS

Didenko, Vladimir V., et al.; Abstract—Detection of Apoptotic DNA Damage in Live Cells Using Fluorescence Resonance Energy Transfer—Development of Molecular Chamelons; Society for Neuorscience (Abstract), vol. 25, p. 2063, 1999.

Maunders, Martin J.; Chapter 10: DNA and RNA Ligases (EC 6.5.1.1, EC 6.5.1.2,and EC 6.5.1.3), Methods in Molecular Biology, vol. 16: Enzymes of Molecular Biology (ed M. M. Burrell); Humana Press, Inc., Totowa, NJ, 1993.

Nikonova, Larisa V., et al.; Properties of some nuclear nucleases of rat thymocytes and their changes in radiation–induced apoptosis; Eur. J. Biochem. 215, pp. 893–901 (1993).

Perez–Sala, Dolores, et al.; Intracellular Alkalinization Suppresses Lovastatin–induced Apoptosis in HL–60 Cells through the Inactivation of a pH–dependent Endonuclease; The Journal of Biological Chemistry, vol. 270 (11), pp. 6235–6242, Mar. 17, 1995.

Saraste, Antti; Morphologic Criteria and Detection of Apoptosis; Herz, vol. 24, pp 189–195 (Nr.3), 1999.

Shiokawa, Daisuke, et al.; Identification of an endonuclease responsible for apoptosis in rat thymocytes; Eur. J. Biochem., vol. 226, pp 23–30, 1994.

Schuman, Stewart, et al.; Characterization of Vaccinia Virus DNA Topolsomerase I Expressed in *Escherichia coli*; The Journal of biological Chemistry, vol. 263 (31), pp 16401–16407, Nov. 5, 1988.

Schuman, Stewart; Site–specific DNA Cleavage by Vaccinia Virus DNA Topoisomerase I—Role of Nucleotide Sequence and DNA Secondary Structure; The Journal of Biological Chemisty, vol. 266 (3), pp 1796–1803, Jan. 25, 1991.

Shuman, Stewart; Communication—Two Classes of DNA End–joining Reactions Catalyzed by Vaccinia Topoisomerase I; The Journal of Biological Chemistry, vol. 267 (24) pp 16755–16758, Aug. 25, 1992.

Schuman, Stewart; Novel Approach to Molecular Cloning and Polynucleotide Synthesis Using Vaccinia DNA Topoisomerase; The Journal of Biological Chemisty, vol. 269 (51) pp 32678–32684, Dec. 23, 1994.

Sikorska, Marianna, et al.: Endonuclease Activities and Apoptosis; Chapter 7 When Cells Die. pp 214–242, (ed R. A. Lockshin, Z. Zakevz, and G. L. Tilly), Willey–Liss, Inc., New York, 1998.

Staley, Kristina, et al.; Apoptotic DNA fragmentation is detected by a Semi–quantitative ligation–mediated PCR of blunt DNA ends; Cell Death and Differentiation (1997) 4, 66–75.

Walker, P. Roy, et al.; Neither Caspase–3 nor DNA Fragmentation Factor Is Required for High Molecular Weight DNA Degradation in Apoptosis; Annals New York Academy of Sciences, 887:48–59 (1999).

Widlak, Piotr, et al.; Cleavage Preferences of the Apoptotic Endonuclease DFF40 (Caspase–activated DNase or Nuclease) on Naked DNA and Chromatin Substrates; The Journal of Biological Chemistry, vol. 275 (11), pp 8226–8232, Mar. 17, 2000.

Sekiguchi, JoAnn, et al.; Nick Sensing by Vaccinia Virus DNA Ligase Requires a 5'Phosphate at the Nick and Occupancy of the Adenylate Binding Site on the Enzyme; Journal of Virology, vol. 17 (12), pp 9679–9684, Dec. 1997.

Krieser, Ronald J., et al.; The Cloning and Expression of Human Deoxyribonuclease, A Possible Role in Apoptosis; The Journal of Biological Chemistry, vol. 273 (47), pp 30909–30914, Nov. 20, 1998.

Sikder, Devanjan, et al.; Determination of the recognition sequence of *Mycobacterium smegmatis* topoisomerase 1 on mycobacterial genomic sequences; Nucleic Acids Research, vol. 28 (8), 1830–1837, 2000.

Hwang, Young, et al.; DNA Contacts Stimulate Catalysis by a Poxvirus Topoisomerase; The Journal of Biological Chemistry, vol. 274 (14), pp 9160–9168, Apr. 2, 1999.

Cheng, Chonghui, et al.; A Catalytic Domain of Eukaryotic DNA Topoisomerase 1; The Journal of Biiological Chemistry, vol. 273 (19), pp 11589–11595, May 8, 1998.

Sekiguchi, JoAnn, et al.; Covalent DNA Binding by Vaccinia Topoisomerase Results in Unpairing of the Thymine Base 5' of the Scissile Bond; The Journal of Biological Chemistry, vol. 271 (32), pp 19436–19442, Aug. 9, 1996.

Shuman, Stewart, et al.; Intramolecular synapsis of duplex DNA by vaccinia topoisomerase; The EMBO Journal, vol. 16 (21), pp 6584–6589, 1997.

Sekiguchi, JoAnn, et al.; Kinetic Analysis of DNA and RNA Strand Transfer Reactions Catalyzed by Vaccinia Topolsomerase; The Journal of Biological Chemistry, vol. 272 (25), pp 15721–15728, Jun. 20, 1997.

* cited by examiner

SEQUENCE LISTING

```
<160> NUMBER OF SEQ ID NOS: 4

<210> SEQ ID NO 1
<211> LENGTH: 37
<212> TYPE: DNA
<213> ORGANISM: Artificial Sequence
<220> FEATURE:
<223> OTHER INFORMATION: Synthetic Artificial Probe
<220> FEATURE:
<221> NAME/KEY: misc_feature
<222> LOCATION: (12)..(12)
<223> OTHER INFORMATION: n equals FITC-dT

<400> SEQUENCE: 1
aagggacctg cngcaggtcc cttaacgcat atgcgtt                              37

<210> SEQ ID NO 2
<211> LENGTH: 38
<212> TYPE: DNA
<213> ORGANISM: Artificial Sequence
<220> FEATURE:
<223> OTHER INFORMATION: Synthetic Artificial Probe
<220> FEATURE:
<221> NAME/KEY: misc_feature
<222> LOCATION: (31)..(31)
<223> OTHER INFORMATION: n equals Tetramethylrhodamine-dT
<220> FEATURE:
<221> NAME/KEY: misc_feature
<222> LOCATION: (12)..(12)
<223> OTHER INFORMATION: n equals FITC-dT

<400> SEQUENCE: 2
aagggacctg cngcaggtcc cttaacgcat natgcgtt                             38

<210> SEQ ID NO 3
<211> LENGTH: 27
<212> TYPE: DNA
<213> ORGANISM: Artificial Sequence
<220> FEATURE:
<223> OTHER INFORMATION: Synthetic Artificial Probe

<400> SEQUENCE: 3
gcgctagacc tgctgctggt ctagcgc                                         27
```

```
<210> SEQ ID NO 4
<211> LENGTH: 5
<212> TYPE: DNA
<213> ORGANISM: Artificial Sequence
<220> FEATURE:
<223> OTHER INFORMATION: Synthetic Artificial Binding Sequence

<400> SEQUENCE: 4 ccctt                                                                    5
```

VACCINIA TOPOISOMERASES I-BASED ASSAYS FOR DETECTION OF SPECIFIC DNA BREAKS

BACKGROUND OF THE INVENTION

This invention was made using finds obtained from the U.S. Government and the U.S. Government may therefore have certain rights in the invention.

1. Field of the Invention

The invention generally relates to the fields of cell biology and molecular biology. The invention specifically relates to the detection of apoptosis in biological samples.

2. Related Art

Apoptosis is a process of programmed cell death. Necrosis describes the process of cell death that occurs when cells die for reasons other than apoptosis, such as by severe injury. Apoptosis is characterized by chromatic margination, nuclear condensation and fragmentation, condensation of the cell with preservation of the organelles and plasma membrane integrity, fragmentation of the cell with formation of membrane-bound acidophilic globules (apoptotic bodies), preservation of mitochondrial transmembrane potential and DNA strand breaks (Saraste, 1999, PCT Application No. PCT/US97/21271, Darzynkiewicz et al., 1992). The process of apoptosis has been shown to be regulated by intracellular proteases called caspases (Bantel et al., 2001) The activation of caspases in apoptosis precedes DNA degradation and the development of apoptotic morphology (Saraste, 1999). Necrosis is characterized by depletion of intracellular ATP stores, swelling of the cell with disruption of organelles, rupture of the plasma membrane and loss of mitochondrial transmembrane potential and DNA strand breaks (Saraste, 1999, Darzynkiewicz et al., 1992).

The apoptotic process causes cellular DNA cleavage into multiples of approximately 180 base pairs. This cleavage pattern is caused by the cleavage of the nuclear DNA within the linker regions between nucleosomes. The endonucleases responsible for this cleavage have been shown to have properties similar to DNases I and II (PCT Application No. PCT/US97/21271). Necrosis causes cellular DNA to randomly degrade (PCT Application No. PCT/US97/21271).

Various methods have been used in attempts to detect apoptotic cells. These methods include the terminal deoxynucleotidyl transferase (TdT)-mediated biotinylated dUTP nick end labeling (TUNEL) assay to detect 3'OH groups, measurement of DNA content using DNA-specific fluorophores, assessment of the pattern of DNA fragmentation using gel electrophoresis, evaluation of morphological features such as plasma membrane integrity using probes that are unable to cross the plasma membrane, preservation of mitochondrial transmembrane potential assayed by retention of rhodamine 123, preservation of the ATP-dependent lysosomal proton pump assayed by the supravital uptake of acridine orange (Darzynkiewicz et al., 1992). The previous approaches used to detect DNA breaks could detect free 3'OH groups in cleaved DNA using terminal transferase or label stretches of single-stranded DNA with the help of polymerases.

An in situ ligation approach for selective detection of double-strand (ds) DNA breaks of DNase I-type (bearing 3'OH/5'PO$_4$) in cellular DNA was recently introduced (Didenko and Hornsby, 1996; Didenko et al., 1998; Didenko et al., BioTechniques, 1999). The assay relies on T4 DNA ligase based attachment of double-stranded DNA probes with blunt ends or short 3' overhangs to the ends of double-strand (ds) DNA breaks that bear 5'PO$_4$. The ligation reaction occurs directly in tissue section (Didenko and Hornsby, 1996; Didenko et al., 1998; Didenko et al., BioTechniques, 1999) or in live cell culture (Didenko et al., Soc. Neurosci., 1999). The probes used in the labeling reaction can be PCR labeled (Didenko and Hornsby, 1996) or synthesized as hairpin-shaped oligonucleotides (Didenko et al., 1998; Didenko et al., BioTechniques, 1999). Because ligase needs a terminal 5'PO$_4$ in the cellular DNA for attachment of the probe, this assay exclusively detects 5' phosphorylated double strand breaks. An example of a nuclease that can produce such breaks is the key apoptotic nuclease CAD/DFF40 (Widlak et al., 2001).

Several types of DNA breaks are used as markers of apoptosis for detection of apoptotic cells in situ. These breaks in the cellular DNA can possess different terminal configurations. Another type of DNA break is represented by double strand breaks bearing a 5'-OH, which are generated by the ubiquitous DNase II-type lysosomal nucleases (Sikorska and Walker, 1998). DNase II-type nucleases play a role in fundamental biological phenomena such as apoptosis, DNA catabolism, and drug-induced DNA cleavage (Krieser and Eastman, 1998; Barry and Eastman, 1993; Toriglia et al., 1995; Sikorska and Walker, 1998; Bernardi, 1971; Perez-Sala et al., 1995).

However, no ligase can attach the 5'OH end of genomic DNA to the 3'OH end of the probe (Maunders, 1993). Attempting to expand the ligation assay to detection of 5'OH bearing breaks by just adding 5'-phosphates to the probe will not result in labeling of this type of DNA damage due to the probe attachment to 3'OH ends and probe self-ligation.

In the present invention, an approach has been developed for visualization of 5'OH ds DNA breaks directly in tissue sections or in purified cellular DNA in solution, thereby allowing selective detection of a subpopulation of apoptotic cells with DNase II-type fragmentation. The approach also allows the detection of apoptotic cells with DNase I-type and DNase II-type fragmentation simultaneously. The present invention utililizes topoisomerase and combined topoisomerase-ligase-based detection methods to image and analyze specific DNA damage in cells in situ. The importance of selective imaging of individual types of DNA damage is shown by the fact that apoptotic DNase I-type nucleases produce identifiable specific breaks absent in necrotic cells (Didenko and Hornsby, 1996; Didenko et al., 1998). Discrimination of the various types of DNA damage is important in the understanding of the generation and repair of DNA damage, particularly for testing drug toxicity in pharmaceutical production and assessing environmental influences.

Prior to the present invention, there were no methods for the selective detection of a subpopulation of apoptotic cells with DNase II-type fragmentation or for simultaneously detecting DNase I-type fragmentation and DNase II-type fragmentation. The present invention comprises a vaccinia topoisomerase I-based approach to label a double-strand break of DNase II type that bears a 5'OH (Krieser and Eastman, 1998; Barry and Eastman, 1993; Toriglia et al., 1995; Sikorska and Walker, 1998; Bernardi, 1971; Perez-Sala et al., 1995). It also comprises a combination of the ligase and topoisomerase based systems into a single assay, resulting in simultaneous detection of two specific types of DNA damage in situ.

SUMMARY OF THE INVENTION

Therefore, one embodiment of the present invention is to provide methods to detect apoptosis in biological samples.

More particular, the invention is to the detection of DNA damage in apoptotic cells.

An embodiment of the present invention is a method of detecting apoptotic cells in a cellular sample, comprising the steps of: obtaining a cellular sample; contacting the cellular sample with a solution comprising a nucleic acid molecule and a topoisomerase I enzyme, the nucleic acid molecule being cleavable by the topoisomerase I enzyme and ligatable to a 5' OH; and detecting the nucleic acid molecule ligated to a 5' OH of the DNA of the cellular sample, wherein the detection of the nucleic acid molecule ligated to a 5' OH of the DNA of the cellular sample correlates to the presence of apoptotic cells. Specifically, the cellular sample may be a tissue section. The 5' OH may be at an overhang or a recessed end. Yet further, the 5' OH may be at a blunt end.

In another embodiment, the method may further comprise the step of fixing the cellular sample. Yet another embodiment, the nucleic acid molecule may comprises a detectable label, which may be detected by microscopy. Such detectable labels may be selected from the group consisting of enzymes, small molecules, chromophores, fluorophores and radiolabeled materials. In a specific embodiment, the detectable label may be FITC.

In still another embodiment, the nucleic acid molecule may have a topoisomerase I enzyme recognition site and a nick in the opposite strand of DNA and the topoisomerase I enzyme recognition site may be 5'-CCCTT-3' (SEQ ID NO: 4). The nick in the opposite strand of DNA may be directly opposite of the point of cleavage at the recognition site. The cleavage of the nucleic acid molecule by topoisomerase I may form nucleic acid molecule A and nucleic acid molecule B.

In another embodiment, the solution may further comprise a nucleic acid ligase enzyme, wherein nucleic acid molecule B is ligatable to a 5'PO$_4$ and detection of nucleic acid molecule A ligated to a 5'OH of the cellular sample and nucleic acid molecule B ligated to a 5'PO$_4$ of the cellular sample correlates to the presence of apoptotic cells. The 5' OH may be at an overhang or at a recessed end. In another embodiment, the 5' OH may be at a blunt end. The nucleic acid molecule A and nucleic acid molecule B may comprise detectable labels. The detectable labels may be selected from the group consisting of enzymes, small molecules, chromophores, fluorophores and radiolabeled materials. One detectable label may be FITC and the other detectable label may be rhodamine. The nucleic acid ligase enzyme may be T4 DNA ligase.

Another embodiment of the present invention is a method of detecting apoptotic cells in a cellular sample comprising the steps of: isolating DNA from a cellular sample; contacting the DNA with a solution comprising a nucleic acid molecule and a topoisomerase I enzyme, the nucleic acid molecule being cleavable by the topoisomerase I enzyme and ligatable to a 5'OH; and detecting the nucleic acid molecule ligated to a 5'OH of the DNA, wherein the detection of the nucleic acid molecule ligated to a 5'OH of the DNA correlates to the presence of apoptotic cells. The nucleic acid molecule may comprise a detectable label. The detectable label may be selected from the group consisting of enzymes, small molecules, chromophores, fluorophores and radiolabeled materials. More specifically, the detectable label may be FITC. The detecting may be by gel electrophoresis.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF SUMMARY OF THE DRAWINGS

The following drawings form part of the present specification and are included to further demonstrate certain aspects of the present invention. The invention may be better understood by reference to one or more of these drawings in combination with the detailed description of specific embodiments presented herein:

FIG. 2A. The double-hairpin FITC-labeled probe (lane 1) was treated with vaccinia topoisomerase (lane 2) for 1 hr at 37° C., resulting in cleavage into two parts: 14-mer and FITC labeled 23-mer. The cleaved FITC-labeled part of the probe with attached topoisomerase (23-mer+TOPO-I) did not enter the 20% acrylamide gel, and is located in the well; the cleaved unlabeled part of the probe (14-mer) is stained by SYBR Green; the unreacted probe without attached topoisomerase (37-mer) is FITC-labeled. The addition of the 20-mer acceptor hairpin, with 5'OH blunt-ends (lane 3) results in appearance of the FITC-labeled 43-mer, due to ligation to the 23-mer TOPO-activated probe. FIG. 2B. The 38-mer double-hairpin dual-labeled with FITC and rhodamine (lane 1) was reacted with vaccinia topoisomerase for 1 hr at 37° C. and treated with proteinase K (4 $\mu$g for 10 min at 37° C.) to remove the enzyme (lane 2), vaccinia topoisomerase cleaved the double-hairpin producing 23-mer FITC-labeled and 15-mer rhodamine-labeled hairpins; the addition of the 20-mer unlabeled acceptor with 5'OH blunt ends prior to proteinase K treatment results in ligation producing the FITC-labeled 43-mer (lane 3). FIG. 2C. Graded dilutions of a 37-mer oligonucleotide, labeled with a single FITC fluorophore were spotted onto nylon membrane in 0.3 $\mu$L aliquots (spot diameter ~1.3 mm). Images were taken using an Olympus IX-70 microscope and a MicroMax digital videocamera. 1.25 fmol (1.23×10$^{-15}$ mol) of FITC in a spot corresponds to 45×10$^3$ FITC molecules/ per the surface area occupied by a cell nucleus 0.01 mm in diameter (1 mm grid shown in red).

FIG. 3A. DNase I and DNase II treated sections. Sections of the normal bovine adrenal gland were treated with either DNase I, producing 3'OH/5'PO$_4$ blunt-ended breaks or DNase II, producing 3' PO$_4$/5' OH blunt-ended breaks. The vaccinia topoisomerase I and T4 DNA ligase selectively labeled only one type of DNA break. Bar=25 $\mu$m. FIG. 3B. Dexamethasone-treated apoptotic rat thymus. Composite images showing simultaneous dual detection of two types of cuts in the thymic cortical areas undergoing apoptosis. Two images on the right show topoisomerase-stained cortical macrophages (revealing 5'OH double-strand breaks) with engulfed nuclear material. Surrounding thymocytes undergo apoptosis and have 5'PO$_4$ double-strand breaks, located at the periphery of their nuclei. Two images on the left demonstrate co-detection of 5'OH and 5'PO4 double-strand blunt ended breaks in apoptotic thymocytes not ingested by the macrophages. Bar –10 μm.

DETAILED DESCRIPTION OF THE INVENTION

Figure 1:
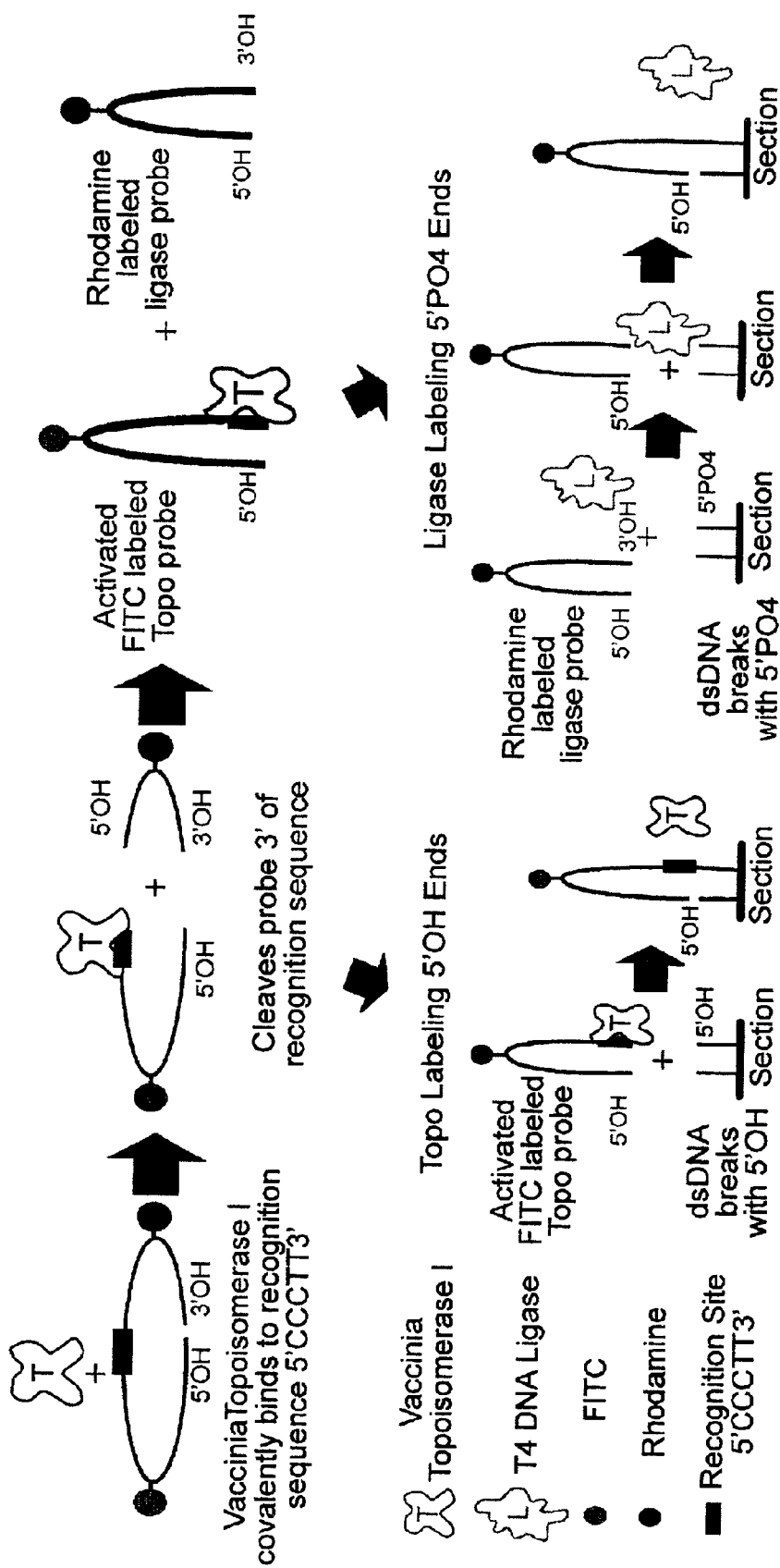
FIG. 1. DNA damage detection in situ using vaccinia topoisomerase I and T4 DNA ligase. Vaccinia topoisomerase I (TOPO) binds to the double-hairpin oligoprobe and cleaves it at the 3' end of the recognition sequence. The TOPO-activated FITC labeled portion of the probe then religates to the blunt-ended DNA breaks that possess a 5'OH in the tissue section. If T4 DNA ligase is added, it ligates the remaining rhodamine-labeled portion of the probe to DNA blunt ends that possess a 5'PO$_4$.

Methods for labeling specific types of DNA damage are important for drug testing, environmental sciences, and biomedical research. Of particular significance is the ability to identify the exact characteristics of DNA damage directly in tissue sections or in cell culture. Several types of DNA breaks are used as markers of apoptosis for detection of apoptotic cells in situ. Examples include DNase I-type and DNase II-type fragmentation of cellular DNA.

As used herein, the term "another nucleic acid" refers to a molecule (i.e., a strand) of DNA, RNA or a derivative or analog thereof, comprising a nucleobase that may or not be part of the same strand as a first nucleic acid.

As used herein, the term "apoptosis" refers to programmed cell death.

As used herein, the term "cellular sample" refers to a representative portion, made up of one or more cells, of a population of cells.

As used herein, the term "chromophore" refers to a molecule comprising a chemical group that absorbs light at a specific frequency and so imparts color to a molecule.

As used herein, the term "complementary" refers to a nucleic acid that it is capable of base-pairing with another nucleic acid according to the standard Watson-Crick, Hoogsteen or reverse Hoogsteen binding complementarity rules. It also may refer to a nucleic acid comprising a sequence of consecutive nucleobases or semiconsecutive nucleobases (e.g., one or more nucleobase labels are not present in the molecule) capable of hybridizing to another nucleic acid strand or duplex even if less than all the nucleobases base pair with a counterpart nucleobase.

As used herein, the term "DNA having an end characteristic of apoptosis" refers to DNA having a ligatable end. Included are ligatable 3' overhangs, ligatable 5' overhangs ligatable 5' recessed ends and ligatable blunt ends.

As used herein, the term "fluorophore" refers to a molecule comprising a chemical group that has luminescence that is caused by the absorption of radiation at one wavelength followed by nearly immediate reradiation usually at a different wavelength and that ceases almost at once when the incident radiation stops.

As used herein, the term "ligation" refers to the process of forming phosphodiester bonds between two nucleic acid fragments. To ligate the DNA fragments together, the ends of the DNA fragments must be compatible with each other.

As used herein, the term "moiety" refers to a smaller chemical or molecular component of a larger chemical or molecular structure.

As used herein, the term "nucleic acid" refers to a molecule (i.e., a strand) of DNA, RNA or a derivative or analog thereof, comprising a nucleobase. The term nucleic acid encompass the terms oligonucleotide and polynucleotide, each as a subgenus of the term nucleic acid. These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or complement(s) of a particular sequence comprising a molecule. As used herein, a single stranded nucleic acid may be denoted by the prefix "ss," a double stranded nucleic acid by the prefix "ds," and a triple stranded nucleic acid by the prefix "ts."

As used herein, the term "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in a manner that may substitute for naturally occurring nucleobase pairing (e.g., the hydrogen bonding between A and T, G and C, and A and U). One skilled in the art realizes that a nucleobase may be comprised in a nucleoside or nucleotide, using any chemical or natural synthesis method described herein or known to one of ordinary skill in the art.

As used herein, the term "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring. Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

As used herein, the term "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'-or 5'-position of the 5-carbon sugar. However, other types of attachments are known in the art, particularly when a nucleotide comprises derivatives or analogs of a naturally occurring 5-carbon sugar or phosphorus moiety.

As used herein, the term "nucleic acid analogs" refers to a derivative or analog of a nucleobase, a nucleobase linker moiety and/or backbone moiety that may be present in a naturally occurring nucleic acid. Derivative refers to a chemically modified or altered form of a naturally occurring molecule, while the terms mimic or analog refer to a molecule that may or may not structurally resemble a naturally occurring molecule or moiety, but possesses similar functions. Nucleobase, nucleoside and nucleotide analogs or derivatives are well known in the art, and have been described (see for example, Scheit, 1980, incorporated herein by reference).

As used herein, the term "necrosis" refers to cell death that is unprogrammed.

As used herein, the term "oligonucleotide" refers to a molecule of greater than about 3 nucleobases in length.

As used herein, the term "oligonucleotide duplex" refers to a length of nucleotides wherein each nucleotide is bound to a nucleotide on the opposite strand of DNA.

As used herein, the term "opposite strand of DNA" refers to DNA that is at least partially complementary to a given length of DNA and may or may not be base paired at each nucleotide or contiguously linked to the given length of DNA by phosphodiester bonds.

As used herein, the terms "purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, caboxyalkyl, amino, hydroxyl, halogen (i.e., fluoro, chloro, bromo, or iodo), thiol or alkylthiol moeity.

As used herein the specification, "a" or "an" may mean one or more. As used herein in the claim(s), when used in conjunction with the word "comprising", the words "a" or "an" may mean one or more than one. As used herein "another" may mean at least a second or more.

A. Detection of DNase II Type Fragmentation

Typically, in situ ligation is used for selective detection of double-strand (ds) breaks in cellular DNA with blunt ends or short 3' overhangs to the ends of ds DNA breaks of DNase I type (bearing 3' OH/5'PO$_4$). It is understood that breaks in cellular DNA can possess different terminal configurations. Another specific type is represented by double strand breaks bearing a 5'-OH, which are generated by the ubiquitous DNase II-type lysosomal nucleases (Sikorska and Walker, 1998). DNase II-type nucleases play a role in fundamental biological phenomena such as apoptosis, DNA catabolism, and drug-induced DNA cleavage (Perez-Sala et al., 1995; Bernardi, 1971; Sikorska and Walker, 1998; Krieser and Eastman, 1998).

A specific embodiment of the present invention is a new approach for visualization of 5'OH ds DNA breaks directly in tissue sections, thereby allowing selective detection of a subpopulation of apoptotic cells with DNase II-type fragmentation. The approach can also be applied to the detection of DNA breaks in purified cellular DNA in solution.

In specific embodiments, the present invention utilizes the unusual enzymatic properties of vaccinia DNA topoisomerase I, a virus-encoded eukaryotic type I topoisomerase. This enzyme binds to duplex DNA having the CCCTT3' recognition sequence, and creates a nick at its 3' end (Shuman, 1991). The enzyme then seals the nick religating the strand back to the acceptor DNA end with 5'OH. If the pentapyrimidine recognition motif is located 2 to 10 bases from the 3' end of the oligonucleotide duplex, the resulting cleaved upstream part of the oligonucleotide, which is now only 2–10 bases long, can dissociate from the duplex. This results in an oligonucleotide with a 2–10 base 3' recessed end. Vaccinia topoisomerase I, which remains bound to the CCCTT motif, then religates the new 3' recessed end to any acceptor DNA possessing a complimentary 5'OH overhang (Shuman, 1994).

The double-strand oligonucleotides with the recognition sequence positioned 2–10 bases from 3'end are activated by vaccinia topoisomerase I, and are able to specifically detect 5'OH overhangs or 5' OH recessed ends.

The inventors of the present invention recognize that blunt ends in cellular DNA are the most advantageous targets for detection, as they represent the most frequent type of ds DNA breaks in apoptosis (Staley et al., 1997). Therefore, the nucleic acid probe molecule design of the present invention was modified to detect blunt-ended DNA breaks. Although vaccinia topoisomerase I can not produce a blunt end by direct cleavage of a single-stranded DNA 3' overhang (Shuman, 1991), placement of a nick in the opposing DNA strand directly against a cleavable bond on a scissible strand, results in generation of blunt-ended probes. It is also envisioned that probes with 3' overhangs can also be produced using the same approach.

Topoisomerase I is used in the present invention to provide endonuclease and ligase activity. It is further envisioned that other enzymes with endonuclease activity may be suitable for use in the present invention.

1. Preparation of Nucleic Acid Molecules

The present invention uses nucleic acid probe molecules. One skilled in the art will readily appreciate that the nucleic acid probe molecules can be RNA or DNA probe molecules. Yet further, it is also understood by those of skill in the art that the ligase enzymes can be easily substituted for one another depending upon if an RNA or DNA probe molecule is used in the present invention.

In the present invention, nucleic acid probe molecules may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemical synthesis using phosphotriester, phosphite or phosphoramidite chemistry and solid phase techniques such as described in EP 266,032, incorporated herein by reference, or via deoxynucleoside H-phosphonate intermediates as described by U.S. Pat. Ser. No. 5,705,629, which is incorporated herein by reference. One of the best known methods for the synthesis of nucleic acids is the polymerase chain reaction (referred to as PCR™) which is described in detail in U.S. Pat. Nos. 4,683,195, 4,683,202 and 4,800,159, and in Innis et al., 1990, each of which is incorporated herein by reference in their entirety.

In further embodiments of the present invention, the nucleic acid probe may be purified on polyacrylamide gels, cesium chloride centrifugation gradients, or by any other means known to one of ordinary skill in the art (see for example, Sambrook et al., 1989, incorporated herein by reference). Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography.

2. Labeled Nucleic Acid Molecule

The nucleic acid probe molecule of the present invention may contain a detectable label. This label may be, for example, a chromophore or radiolabel. In another embodiment, the probe incorporates a fluorescent dye or label. In other embodiments, the probe is conjugated to a binding partner, such as an antibody or biotin, where the other member of the binding pair carries a detectable moiety. In yet other embodiments, the probe has a mass label that can be used to detect the molecule amplified. In still other embodiments, solid-phase capture methods combined with a standard probe may be used as well.

The detection of nucleic acid probe molecules will be performed using art recognized methods. For example, the nucleic acid probe molecule may incorporate a detectable label that can be directly detected. In this embodiment, the detectable label may be a chromophore, fluorophore, enzyme or small molecule.

In an embodiment of the present invention, the nucleic acid probe molecules will include detectable labels that are fluorophores. Examples of suitable fluorophores include, but are not limited to, fluorescein isothiocyanate (FITC), rhodamine, 4',6-Diamidino-2-phenylindole dihydrochloride (DAPI), Texas Red™, N-hydroxysuccinimidyl 1-pyrenebutyrate (PYB), eosin and N-hydroxysuccinimidyl 1-pyrenesulfonate (PYS).

In an alternative embodiment, the nucleic acid probe molecules will include detectable labels that can be bound by a reagent comprising a molecule having a binding portion and a signaling portion. Examples of suitable binding portions include, but are not limited to, avidin, streptavidin, antibodies, and antibody fragments. Embodiments include a detectable label that is a bromine atom incorporated into a nucleic acid probe molecule and a binding portion that comprises an anti-bromine antibody. Other embodiments include detectable labels that are biotin or biotin analogs and binding portions that comprise avidin or streptavidin. Yet further, embodiments may utilize digoxygenin as a detectable label and a binding portion that comprises an anti-digoxygenin antibody or antibody fragment.

In embodiments that utilize a reagent that comprises a molecule that binds to a detectable label, the molecule may also comprise a signaling portion that permits detection of the presence of the reagent. For example, the reagent may comprise a molecule having a binding portion that binds to the detectable label, and the molecule may additionally comprise a signaling portion that permits detection of the molecule. Examples of signaling portions include enzymes, chromophores, fluorophores, and radio labeled material. Thus, the molecule may comprise a binding portion covalently attached to a signaling portion. Examples include, but are not limited to, avidin or streptavidin covalently attached to enzymes, such as luciferases, peroxidases, galactosidases, glucuronidases, and phosphatases. Embodiments can use streptavidin covalently attached to horseradish peroxidase. Other examples include antibodies coupled directly with enzymes. Those skilled in the art are aware that such coupling may be accomplished using a variety of coupling reagents such as those sold by Pierce Chemical Co. of Rockford, Ill. Examples include anti-bromine antibody coupled to enzymes such as horseradish peroxidase.

In some embodiments of the instant invention, detection of the detectable label is accomplished by contacting the detectable label with a reagent that comprises a first molecule that binds to the detectable label and then subsequently applying a reagent that comprises a second molecule that binds to the first molecule. For example, when the detectable molecule is bromine, the sample may be contacted with a reagent that comprises an anti-bromine antibody or antibody fragment. The sample may then be contacted with a reagent that comprises a second molecule that binds to the anti-bromine antibody or antibody fragment. Examples include, but are not limited to, reagents comprising protein A, lectins, and antibodies that bind to the anti-bromine antibody coupled to a signaling portion. The second molecule may contain a signaling portion. The signaling portion may include an enzyme, chromophore, fluorophore, or radio-labeled material. The preparation and utilization of such second molecules are well known to those skilled in the art. (See, Sambrook, et al.) Other examples include the use of biotin or biotin analogs as detectable labels, streptavidin or avidin as first molecules, and anti-streptavidin or anti-avidin antibody or antibody fragments coupled to signaling portions as second molecules. Other embodiments utilize digoxygenin as detectable labels, anti-digoxygenin antibodies as first molecules, and antibodies directed against the anti-digoxygenin antibodies coupled to signaling portions as second molecules.

In embodiments that utilize a first binding molecule to bind a detectable label and a second molecule to bind the first molecule, the second molecule may contain a signaling portion. The signaling portion may be any signaling portion known in the art. Signaling portions of the present invention include, but are not limited to, chromophore, fluorophores, enzymes, and radio-labeled material. When the signaling portion is a chromophore or fluorophore, the presence of the signaling portion may be detected visually or with the use of devices that measure optical density. When utilizing optical density readers, it may be desirable to place the sample on or in a solid support that is transparent at the wavelength at which the chromophore absorbs or at the wavelengths at which excitation and emission of the fluorophore occur. This methodology may be useful to quantify the presence of termini generated by specific nucleases. Transparent solid supports are seen to include, but are not limited to, transparent test strips and microtiter plates.

When the signaling portion is an enzyme, the method will include a step of providing the enzyme with a substrate. The substrate may be provided as part of the reagent comprising the second molecule. Alternatively, the substrate may be provided after the reagent comprising the second molecule. When the enzyme reacts with the substrate, some measurable change must take place. For example, the enzyme may convert a colorless substrate molecule into a colored product molecule. Alternatively, a colored substrate molecule may be converted into a colorless product molecule. In some instances, one of the products of the enzyme reaction may be a photon of light. In these instances, the quantity of photons of light produced can be measured. The available enzymes and appropriate substrates and quantitative methodologies are well known to those skilled in the art.

The type of label incorporated may depend on the method used for analysis. When using capillary electrophoresis, microfluidic electrophoresis, HPLC, or LC separations, either incorporated or intercalated fluorescent dyes are used to label and detect the nucleic acid. Samples are detected dynamically, in that fluorescence is quantitated as a labeled species moves past the detector. If polyacrylamide gel or slab gel electrophoresis is used, the nucleic acid can be labeled with a small molecule, fluorophore, a chromophore or a radioisotope, or by associated enzymatic reaction. Examples of small molecules include, but are not limited to, digoxigenin, biotin and bromine. Examples of fluorophores include, but are not limited to, fluorescein isothiocyanate (FITC), rhodamine, Texas Red™, N-hydroxysuccinimidyl 1-pyrenebutyrate (PYB), eosin and N-hydroxysuccinimidyl 1-pyrenesulfonate (PYS). Examples of chromophores include, but are not limited to, fluorescein, rhodamine or eosin. A chromophore may or may not be fluorescent as well. Examples of radioisotopes include, but are not limited to, $^{32}P$, $^{125}I$ and $^{35}S$.

Enzymatic detection involves binding an enzyme to the nucleic acid, e.g., via a biotin:avidin interaction, following separation of products on a gel, then detection by chemical reaction, such as chemiluminescence generated with luminol. Examples of enzymes include, but are not limited to, phosphatases, galactosidases, glucuronidases, peroxidases and luciferases. A fluorescent signal can be monitored dynamically. Detection with a radioisotope or enzymatic reaction may require an initial separation by gel electrophoresis, followed by transfer of DNA molecules to a solid support (blot) prior to analysis. If blots are made, they can be analyzed more than once by probing, stripping the blot, and then reprobing. If products are separated using a mass spectrometer, detection involves identifying if the sample contains a peak of the correct mass to charge ratio for the nucleic acid molecule ligated to the 5'OH of the cellular sample and any label that is attached.

If detection is by microscopy, different types and methods of microscopy could be used. Examples include, but are not limited to, light microscope (brightfield microscopy, phase-contrast and differential interference contrast (DIC or Nomarski), laser scanning confocal and fluorescence. For example, in fluorescence microscopy, light is filtered through an excitation filter to excite the fluorophore. The fluorophore then emits light at a wavelength longer than the excitation wavelength. This light is then collected and depicts the location of the fluorophore.

3. Sample Preparation a. Cellular Samples

Cells may be in live cell culture or tissue section and may or may not be fixed prior to analysis for the presence of apoptotic cells. Suspended cells can be fixed upon glass slides using standard fixing techniques, such as paraformaldehyde or buffered formaldehyde.

In certain embodiments, the cellular sample may be composed of a subpopulation of cells or an entire tissue. The cellular sample may comprise, but is not limited to, at least one of the following: adrenal gland, thymus, adipocytes, alveolar, ameloblasts, axon, basal cells, blood (e.g., lymphocytes), blood vessel, bone, bone marrow, brain, breast, cartilage, cervix, colon, cornea, embryonic, endometrium, endothelial, epithelial, esophagus, facia, fibroblast, follicular, heart, ganglion cells, glial cells, goblet cells, kidney, liver, lung, lymph node, muscle, neuron, ovaries, pancreas, peripheral blood, prostate, skin, skin, small intestine, spleen, stem cells, stomach, testes, and thymus.

b. Tissue Samples

In preferred embodiment, the sample is a tissue sample. The tissue may be part or separated from an organism. In certain embodiments, a tissue may comprise, but is not limited to, adrenal glands, adipose, alveolar, axon, blood vessel, bone, bone marrow, brain, breast, cartilage, cervix, colon, cornea, embryonic, endometrium, endothelial, epithelial, esophagus, facia, fibroblast, follicular, heart, kidney, liver, lung, lymph node, muscle, neuron, ovaries, pancreas, peripheral blood, prostate, skin, skin, small intestine, spleen, stomach, testes, and thymus.

Tissues may be fixed in 4% paraformaldehyde. If a well-vascularized organ is to be fixed, it is suggested that the whole animal be perfused with the fixative prior to harvesting the organ. After incubating 18 hours in paraformaldehyde, the tissue fragments may be placed in 70% ethanol, and then taken through graded alcohols to 100% ethanol. It is important that fixation does not block probe access. They may be placed overnight in chloroform and embedded in paraffin.

Sections may be treated with xylene to remove the paraffin and rehydrated in graded alcohol concentrations. The rehydration may be accomplished by incubating the sample in xylene for 5 minutes then replacing the xylene with fresh xylene and incubating a second 5 minute interval. The xylene may be removed and the sample incubated in 100% ethanol for 5 minutes. The ethanol may then be removed and fresh 100% ethanol added. The sample may be incubated for an additional 5 minutes in 100% ethanol. The ethanol may then be replaced with 96% ethanol and the sample incubated for 30 seconds. The 96% ethanol may then be replaced with 80% ethanol and the sample incubated for 30 seconds. The 80% ethanol may then be removed and the sample washed in water.

Sections may be washed in water and preblocked with BSA. The blocking solution may be aspirated, and the reaction mixture containing the probe and vaccinia topoisomerase I, or other enzyme with ligase activity, may be applied to sections. Acetylation of tissue samples is commonly used to decrease background binding of radioisotope labels. The sections may be incubated in a humidified chamber, washed in water, rinsed with sodium bicarbonate, covered with Vectashield with DAPI and coverslipped.

Detection of the bound probe and label is dependent upon the type of label used. For example, radioactive labels may be detected using autoradiography and fluorophore labels may be detected by fluorescence microscopy. One skilled in the art would be aware of the method of detection to use for each label.

B. Analyzing DNA to Determine Types of Termini

The termini produced by various nuclease enzymes have previously been determined. By determining the types of termini present in a DNA sample, it is possible to gain information about the nuclease enzymes that have acted upon the DNA. To determine if the DNA in a given sample has been acted upon by a nuclease, the DNA is probed with various nucleic acid fragments. Each nucleic acid fragment used as a probe will have termini capable of ligating to the termini produced by a specific type of nuclease. By determining which fragment can be ligated to the DNA sample, it is possible to determine what nuclease has acted upon the sample. This process may be conducted by dividing the sample into aliquots and probing each aliquot with a different fragment. Alternatively, multiple fragments may be tested simultaneously on the same sample. In this case, the fragments may be distinguished from each other by the incorporation of different detectable labels. The detectable labels may be enzymes, small molecules, chromophores, fluorophores, or radiolabeled materials. Those skilled in the art can readily select suitable detectable labels so as to permit the simultaneous detection of each label. The ligation reaction may be performed on tissue sections or on isolated DNA that has been size fractionated on an agarose gel. The DNA is first transferred to a solid support by any conventional means, i.e., capillary action, vacuum blotting or electroblotting. The solid support is then blocked and the ligation reaction conducted.

The present invention may be used to detect and/or isolate DNA target molecules having deemed overhanging and or recessed termini. This is accomplished by attaching a nucleic acid probe molecule having a defined terminus to a solid support. The solid support may be any solid support known in the art including, but not limited to, membranes, microtiter plates, agarose beads, beads made of a synthetic resin, and any other solid support known in the art.

In an embodiment of the present invention, a number of double stranded nucleic acid probe molecules, can be fixed to different regions of a solid support. A DNA sample suspected of containing termini generated by the action of one or more nucleases, may be brought into contact with the fixed nucleic acid probe molecules in the presence of appropriate topoisomerase and/or ligase enzymes and co-factors (metal ions, ATP, buffers, etc.).

The DNA sample is incubated with the nucleic acid probe molecule at an appropriate temperature of from about 10° C. to about 37° C. for an appropriate length of time of about 30 minutes to about 16 hours. After incubation, the solid support may be washed to remove any unligated DNA and the presence of DNA ligated to the probe molecules is detected.

In an alternative embodiment, an aliquot of the DNA suspected of containing termini created by the action of one or more nuclease enzymes may be fixed to a solid support using any art recognized means, such as, for example, UV treatment. The fixed DNA can then be contacted with a solution containing one or more nucleic acid probe molecules, DNA, RNA, or a mixture of both, and the appropriate ligase enzymes. The probe molecules will be selected to contain detectable labels. The detectable labels will be selected so that each label will be detectable in the presence of the detectable labels present on the other nucleic acid probe molecules and, ideally, all labels will be simultaneously detectable.

After a suitable period of time to permit the ligation of the probe molecules to the DNA termini present in the aliquot, the solid support may be washed and the presence of nucleic acid probe molecules detected.

In one embodiment, DNA present in a sample is isolated according to standard methodologies (see Sambrook, et al.). The DNA is size fractionated on agarose and then transferred to a solid support. The solid support is generally in the form of a membrane. The membrane may be constructed of any commonly utilized materials, such as nylon, PVDF or nitrocellulose. The transfer may be accomplished by any commonly utilized methodologies. These methodologies are considered to include capillary action, vacuum blotting and electroblotting.

After the DNA has been transferred to the solid support, the solid support is blocked using known blocking solutions. Subsequent to blocking, the solid support is contacted with the solution containing a DNA probe molecule specific for a target DNA, a topoisomerase I enzyme, and the requisite co-factors. The ligation reaction may be conducted at a temperature from about 4° C. to about 37° C. Preferably, the ligation reaction may be conducted at a temperature from about 10° C. to about 37° C. and most preferably at a temperature from about 15° C. to 37° C. One skilled in the art will readily recognize that it is necessary to prevent the solid support from drying out during the process of the ligation reaction. In order to accomplish this, the ligation reaction may be conducted in a sealed container, such as, for example, a sealed plastic bag or a roller bottle or any commonly used device known to those skilled in the art. After completion of the ligation reaction, the solid support is washed and the DNA probe molecule is detected as described above. If the dual labeled probe is used, one skilled in the art would be aware of required modifications to the assay.

The nucleic acid probe molecule attached to the solid support is called the capturing fragment. The capturing fragment is selected so as to have a complementary terminus to the defined overhanging and/or recessed terminus of the DNA target molecule. The fragment may be prepared by any means known in the art. For example, the fragment may be prepared from a larger DNA molecule by treatment of the larger molecule with a nuclease that generates the desired overhanging and/or recessed termini. The DNA fragments possessing the desired overhanging and/or recessed termini may then be isolated and subsequently fixed to the solid support, using any methodology known in the art. For example, the solid support may be provided with a reactive functionality that is capable of reacting with functional groups present in the capturing fragment. Alternatively, the capturing fragment may be modified so as to contain a reactive functionality capable of reacting with the solid support. In other embodiments, the capturing fragment will be provided with a small molecule that can be bound by a group present on the solid support. Those skilled in the art will readily appreciate that any methodology that does not affect the overhanging terminus of the capture fragment may be used to fix the capture fragment to the solid support.

The capture fragment may be designed so as to contain additional desirable structural characteristics beyond an overhanging and/or recessed terminus. For example, the capturing fragment may be equipped with a restriction enzyme site. After the capturing fragment has been used to isolate the corresponding nuclease-cleaved DNA, the capturing fragment may be cleaved using a restriction endonuclease, thereby liberating a DNA molecule that includes a portion of the capturing fragment in addition to the nuclease cleaved fragment.

The DNA target molecule can be cloned and sequenced using methodologies well known to those skilled in the art. For example, the nuclease-cleaved DNA can be ligated to the capturing fragment. Subsequently, the solid support may be treated with Pfu polymerase to generate blunt ended fragments attached to the solid support. The solid support may then be treated with a restriction enzyme to cleave the blunt ended fragment from the solid support. The fragment can then be cloned into a vector treated so as to have a blunt end and an end that corresponds to the end generated by the restriction enzyme. Those skilled in the art can readily envision other, equivalent cloning strategies. Alternatively, the capturing fragment may be equipped with a sequence to which a PCR primer will bind. After reaction with the nuclease cleaved DNA, the reaction mixture may be provided with the necessary reagents to perform PCR on the captured nuclease cleaved fragment. It is readily apparent to those skilled in the art that more than one desirable functional characteristics can be incorporated into the capturing fragment. For example, both restriction enzyme cleavage sites and PCR primer binding sites may be incorporated into the same capturing fragment.

The capturing fragment may be provided with a detectable label. After ligating the nuclease cleaved DNA to the capturing fragment, the capturing fragment may be cleaved from the solid support and the presence of the detectable label assayed. It may be necessary to perform a step of isolating capture fragment bound to nuclease cleaved DNA from capture fragment not so bound. Those skilled in the art can readily accomplish this using known methods based upon the difference in size of the two types of fragment.

The DNA suspected of containing nuclease-cleaved ends may be isolated from any source. The DNA is isolated using methodologies readily known by those skilled in the art. After the DNA suspected of containing nuclease cleaved ends is isolated; it is combined with capturing fragment in the presence of DNA ligase and the requisite co-factors, such as divalent metal ions and ATP. After a suitable length incubation, the ligating solution is removed by washing and the presence or absence of nuclease-cleaved DNA can be detected. The basic assay described above can be configured in a variety of ways. For example, the capturing fragment may be provided to the ligation solution as a fragment free in solution. In embodiments of this nature, the capturing fragment will be provided with a binding label, such as biotin or digoxygenin. After a suitable reaction period, a solid support containing a molecule capable of attaching to the binding label, such as avidin, streptavidin, or anti-digoxygenin, is mixed with the solution. After an incubation period to allow the binding label to be attached to the solid support, the solid support can be washed so as to remove unbound material and then treated in any fashion desirable.

Alternatively, the capturing fragment may be provided to the ligation mixture already attached to a solid support. After the ligation reaction is allowed to proceed, the solid support can then be washed as before.

The present invention may be used as an assay to detect termini of a specific overhang or recessed end present in a DNA sample. After the ligation and attachment to a solid support as described above, the sample is washed and then provided with a known quantity of complementary termini. The fragments containing these complementary termini will be detectable in some fashion, for example, as small molecule, radio labeled, fluorophore or chromophore. A second ligation reaction may be performed so as to attach the radio labeled fragments to any remaining overhanging termini that have not bound nuclease treated DNA from the ligation reaction. The more radio labeled material that binds, the fewer correct overhanging termini were present in the original sample.

It is also envisioned that the topoisomerase-based assay of the present invention can be combined with ligase-mediated labeling.

For example, when T4 DNA ligase is added in the reaction mix, the second hairpin, produced by the split of the double-hairpin probe, can be simultaneously ligated by DNA ligase to the breaks with DNase I architecture, bearing 5'PO$_4$ groups. Thus, it is contemplated that the present invention can be used to determine DNase type I and DNase type II fragments simultaneously.

C. EXAMPLES

The following examples are included to demonstrate preferred embodiments of the invention. It should be appreciated by those skilled in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1. Materials and Methods

Oligonucleotides

The probes were prepared by Synthetic Genetics, San Diego, Calif.

Probe 1 (SEQ ED NO: 1). (double-hairpin vaccinia topoisomerase I cleavable probe, single fluorescein labeled (VACC-RC): 5' AAG GGA CCT GCF GCA GGT CCC TTA ACG CAT ATG CGT T 3'; F-FITC-dT.

Probe 2 (SEQ ID NO: 2). (double-hairpin vaccinia topoisomerase I cleavable probe, dual labeled with fluorescein and rhodamine (VACC-RC DUAL): 5' AAG GGA CCT GCF GCA GGT CCC TTA ACG CAT RAT GCG TT 3'; F-FITC-dT, R-Tetramethylrhodamine-dT.

Oligo 1 (SEQ ID NO: 3). (hairpin for reaction testing in solution as the source of blunt ends): 5' GCG CTA GAC CTG CTG CTG GTC TAG CGC 3'.

Tissue Preparation of Apoptotic Thymus

Sprague-Dawley rats (150 g) were injected subcutaneously with 6 mg/kg dexamethasone (Sigma) dissolved in 30% dimethyl sulfoxide in water. Animals were sacrificed after 24 h and the thymus was fixed in 4% paraformaldehyde. After incubating 18 hours in paraformaldehyde, the tissue fragments were placed in 70% ethanol, and then taken through graded alcohols to 100% ethanol. They were placed overnight in chloroform and embedded in paraffin.

6-$\mu$m sections were treated with xylene to remove the paraffin and rehydrated in graded alcohol concentrations. The rehydration was accomplished by incubating the sample in xylene for 5 minutes then replacing the xylene with fresh xylene and incubating a second 5 minute interval. The xylene was removed and the sample was incubated in 100% ethanol for 5 minutes. The ethanol was then removed and fresh 100% ethanol was added. The sample was incubated for an additional 5 minutes in 100% ethanol. The ethanol was then replaced with 96% ethanol and the sample was incubated for 30 seconds. The 96% ethanol was then replaced with 80% ethanol and the sample was incubated for 30 seconds. The 80% ethanol was then removed and the sample washed in water.

Example 2. Vaccinia Topoisomerase I-based Labeling of DNA Ends in Solution

Reaction mixture (10 $\mu$l) containing 50 mM Tris-HCl (pH 7.4), 100 pmol of probe 1 (SEQ ID NO: 1) (VACC-RC) or probe 2 (SEQ ID NO: 2) (VACC-RC DUAL), 100 pmol oligo 1 (SEQ ID NO: 3), 150 pmol (1.2 $\mu$g/$\mu$l) vaccinia topoisomerase I was incubated for 1 hr at 37°. The samples were electrophoresed through a 20% polyacrylamide gel for 90 min at 180 V, and stained with SYBR Green (Molecular Probes).

Example 3. Vaccinia Topoisomerase I-based Labeling of DNA Ends in Tissue Sections The new approach utilizes the unusual enzymatic properties of vaccinia DNA topoisomerase I, a virus-encoded eukaryotic type I topoisomerase. This enzyme binds to duplex DNA having the 5'CCCTT3' (SEQ ID NO: 4) recognition sequence, and creates a nick at its 3' end (Shuman, 1991). The enzyme then seals the nick religating the strand back to the acceptor DNA end with 5'OH. If the pentapyrimidine recognition motif is located 2 to 10 bases from the 3' end of the oligonucleotide duplex, the resulting cleaved upstream portion of the oligonucleotide, which is now only 2–10 bases long, can dissociate from the duplex (Shuman, 1994). This results in an oligonucleotide with a 2–10 base 3' recessed end. Vaccinia topoisomerase I, which remains bound to the CCCTT (SEQ ID NO: 4) motif, then religates the new 3' recessed end to any acceptor DNA possessing a complimentary 5'OH overhang (Shuman, 1994).

Thus, double-strand oligonucleotides with the recognition sequence positioned 2–10 bases from the 3'end are activated by vaccinia topoisomerase I, and should be able to specifically detect 5'OH overhangs. However, blunt ends in cellular DNA are the most advantageous targets for detection, as they represent the most frequent type of ds DNA breaks in apoptosis (Staley et al., 1997). Therefore, the probe design was modified to detect blunt-ended DNA breaks. Although vaccinia topoisomerase I can not produce a blunt end by direct cleavage of a single-stranded DNA 3' overhang (Shuman, 1994), placement of a nick in the opposing DNA strand directly against a cleavable bond on a scissible strand, results in generation of blunt-ended probes (FIG. 1). Blunt-ended oligonucleotide duplexes, similarly activated by vaccinia topoisomerase, were shown to specifically ligate to the blunt-ended acceptor (Shuman, 1992). In principle, the probes with 3' overhangs (recessed 5' ends) can also be produced using the same approach.

Figure 2:
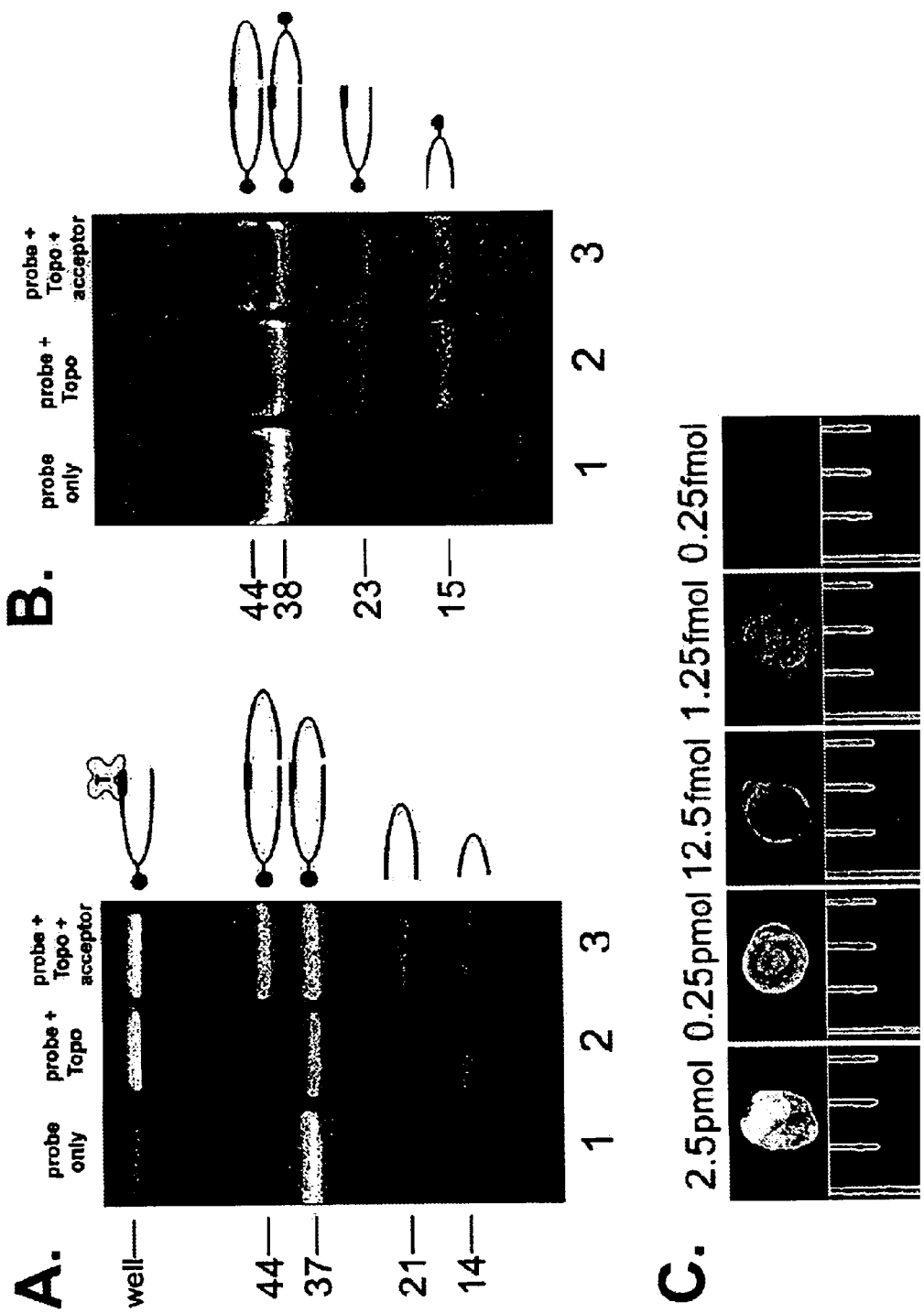
FIG. 2A–FIG. 2C. Detection of blunt-ended 5'OH bearing DNA ends in solution using a double-hairpin probe.

In the assay, the inventors positioned the recognition sequence in the central part of a double hairpin oligonucleotide, having a nick located opposite the vaccinia topoisomerase I cleavable bond (FIG. 1). Mixing the probes with vaccinia topoisomerase I results in rapid preparation of an active enzyme-oligonucleotide complex ligatable to the blunt-ended breaks in target DNA (FIG. 1 and FIG. 2).

6 µm thick sections of the normal bovine adrenal gland were deparaffinized with xylene, rehydrated in graded alcohol concentrations, washed in water, and treated with proteinase K (50 µg/ml) for 15 minutes at room temperature (23° C.). Sections were washed in water (2×10 min), and treated with 100 ng/µl of DNase I (Roche, Indianapolis, Ind.) in 50 mM Tris-HCL, pH 7.4, 10 mM $MgCl_2$ overnight at 37° C., or with 500 ng/µl DNase II in the buffer supplied with the enzyme (Sigma Chemicals, St. Louis, Mo.) for 30 min at 37° C. Sections were washed in water (3×10 min), and preblocked with 2% BSA (15 min, 23° C.). The blocking solution was aspirated, and the reaction mixture (25 µl) containing 50 mM Tris-HCL, PH 7.4, 100 pmol probe 1 (SEQ ID NO: 1) (VACC-RC), 15% PEG-8000, 215 pmol vaccinia topoisomerase I was applied to sections. The sections were incubated 1 hour at 37° C. in a humidified chamber, washed in water (3×10 min), rinsed with sodium bicarbonate, covered with Vectashield with DAPI (Vector Laboratories, Burlingame, Calif.) and coverslipped.

Figure 3:
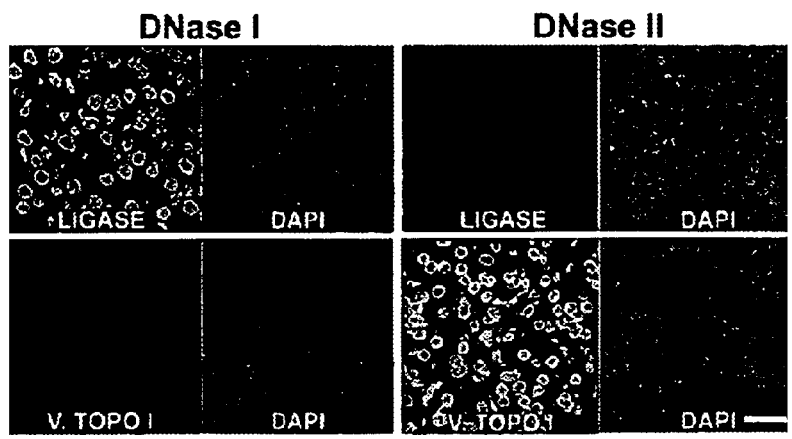
FIG. 3A–FIG. 3B. DNA damage detection in tissue sections using vaccinia topoisomerase I and its combination with T4 DNA ligase.
Figure 3:
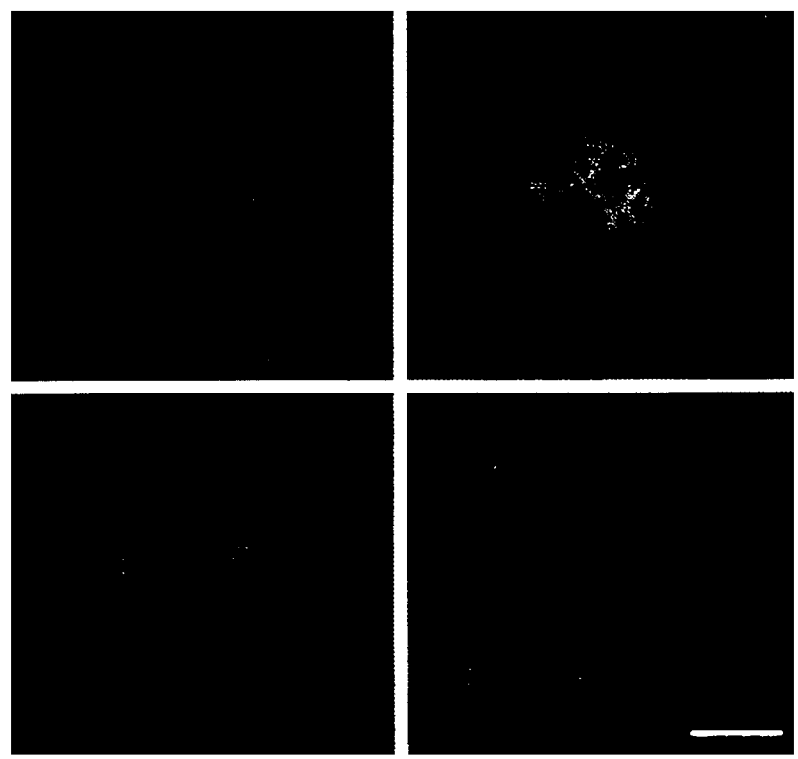

The cleavage and re-ligation of the probe to a blunt-ended acceptor with a 5'OH end was verified in solution (FIG. 2A), and then tested in tissue section format detecting DNase II but not DNase I cuts (FIG. 3A).

The number of breaks in apoptosis rises from about 50.000 per genome at the initial high molecular weight DNA degradation to $3×10^6$ during internucleosomal DNA fragmentation stage (Walker et al., 1999). The new assay places a single FITC fluorophore at the end of each DNA break. Observation of the results of this labeling reaction is well within the limits of the regular fluorescent microscope. As an illustration, using a dot spot test the inventors verified that the optical system (Olympus IX-70 microscope with MicroMax digital videocamera) can visualize 1.25 fmole of FITC spotted as a 1.3 mm dot, which corresponds to ~45.000 FITC molecules per the surface area occupied by a nucleus 0.01 mm in diameter (FIG. 2C). The visualization of smaller numbers of breaks generated without apoptosis using a similar optical system might require a biotin-labeled probe with enzymatic amplification of signal or confocal microscopy, capable of detecting a single fluorophore molecule per cell (Byassee et al., 2000).

Example 4. Combined Vaccinia Topoisomerase I-T4 DNA Ligase-based Labeling of DNA Ends in Tissue Sections Though the new topoisomerase-based assay can be used on its own, it can also be combined with ligase-mediated labeling. When T4 DNA ligase is added in the reaction mix, the second hairpin, produced by the split of the double-hairpin probe, can be simultaneously ligated by DNA ligase to the breaks with DNase I architecture, bearing $5'PO_4$ groups (FIG. 1). The dual labeled probe bearing fluorophores on both hairpins was tested in solution with vaccinia topoisomerase (FIG. 2B). The combined assay using both topoisomerase and ligase was then tested in tissue sections of dexamethazone-treated rat thymus detecting the primary DNase I-like cleavage in apoptotic thymocytes nuclei and DNase II-like breaks in the cytoplasm of cortical macrophages, ingesting apoptotic cells. Interestingly some apoptotic thymocytes not ingested by the macrophages demonstrated appearance of both 5'OH and 5' PO4 breaks (FIG. 3B).

The primary type of DNA cleavage in dexamethasone-treated thymus has been determined to be of DNase I type (Shiokawa et al., 1994). DNase II type breaks generated during lysosomal digestion of phagocytized apoptotic cells were known to exist, but have not been detected before using biochemical bulk DNA purifications (Shiokawa et al., 1994; Nikonova et al., 1993). DNase II type cuts in the nuclear extracts of thymocytes were detected only under the optimal conditions and attributed to DNase II-like nuclease (Nikonova et al., 1993). The new approach, being an in situ technique, visualizes both DNase I- and II-type breaks even in small numbers of cells and thus increases the sensitivity of DNA damage detection.

6 µm thick sections of dexamethasone treated rat thymus were deparaffinized with xylene, rehydrated in graded alcohol concentrations, washed in water, and treated with proteinase K (50 µg/ml) for 15 minutes at room temperature (23° C.). After two 10 min washes in water, the sections were blocked with 2% BSA for 15 min at 23° C. The solution was aspirated and reaction mix (25 µl) containing 66 mM Tris HCl, pH 7.5, 5 mM $MgCl_2$, 0.1 mM dithioerythritol, 1 mM ATP, and 15% polyethylene glycol-8000, 70 pmol (900 ng) probe 2 (SEQ ID NO: 2) (VACC-RC DUAL), 215 pmol vaccinia topoisomerase I and 10 units T4 DNA ligase (500 U/ml) was applied to the sections. The sections were incubated in a humidified box (1 hr at 23° C.). They were then briefly washed in water. Sections were then counterstained with 4,6-diamidino-2-phenylindole (DAPI).

In a mock reaction, no signal was observed, when an equal volume of 50% glycerol in water was substituted for T4 DNA ligase, and vaccinia topoisomerase I was deactivated by preincubation with 4 µg of proteinase K for 10 min at 23° C. The proteinase K was subsequently inactivated by boiling. Control sections of normal bovine adrenal and normal rat thymus were unstained after ligase-mediated labeling (beyond a couple of apoptotic cells in the thymus) (Didenko and Hornsby, 1996). No signal was detected in control series, after the pretreatment with 215 pmoles of vaccinia topoisomerase I for 2 hours at 37° C.

Images were captured using an Olympus IX-70 fluorescent microscope and a MicroMax digital videocamera (Princeton Instruments, Inc.). Composite images were created in MetaMorph 4.1 (Advanced Scientific, Inc.). (Chroma Technology bandpass filter set was used: FITC excitation D490/40, emission 520/10; rhodamine excitation D560/40, emission 620/30, DAPI excitation D360/40, emission 460/20).

References

The following references, to the extent that they provide exemplary procedural or other details supplementary to those set forth herein, are specifically incorporated herein by reference.

U.S. Pat. No. 5,296,375
U.S. Pat. No. 5,856,174
U.S. Pat. No. 5,904,824
U.S. Pat. Nos. 5,304,487
WO 94/05414
Bantel, et al., *Eur J Cell Biol* 80:230–9, 2001.
Barry, and Eastman, *Arch. Biochem. Biophys.* 300, 440–450, 1993.
Berkenkamp S, et al., *Science,* 281(5374):260–2, 1998.
Bernardi, G. Spleen Deoxyribonuclease. In *The Enzymes,* (ed Boyer, P. D.), v. 4, 271–287 (Academic Press, New York; 1971).
Byassee et al, *Anal Chem* 72:5606–11(2000).
Darzynkiewicz et al., *Cytometry* 13:795–808, 1992.
Didenko and Hornsby, *J. Cell Biol.* 135, 1369–1376 (1996).
Didenko et al., *BioTechniques* 27, 1130–1132 (1999).
Didenko et al., *Am. J. Pathol.* 152,897–902 (1998).
Didenko et al., *Soc Neurosci Abst* 25,2063 (1999).
Freifelder, *Physical Biochemistry Applications to Biochemistry and Molecular Biology,* 2nd ed. Wm. Freeman and Co., New York, N.Y., 1982.
Krieser and Eastman *J. Biol. Chem.,* 273, 30909–30914 (1998).
Maunders, M. J. In *Enzymes of Molecular Biology.* (ed Burrel, M. M.) 213–230 (Humana Press, Totowa; 1993).
Nikonova et al., *Eur. J. Biochem.* 215:893–901 (1993).
Perez-Sala et al., *J. Biol. Chem.* 270, 6235–6242 (1995).
Sambrook et al., "Molecular Cloning," *A Laboratory Manual,* 2d Ed., Cold Spring Harbor Laboratory Press, New York, 13.7–13.9:1989.
Saraste, *Herz* 24:189–95, (1999).
Shiokawa et al., *Eur J Biochem* 226:23–30 (1994).
Shuman, *J. Biol.Chem.* 263, 16401–16407 (1988).
Shuman, *J. Biol.Chem.* 266, 1796–1803 (1991).
Shuman, *J. Biol.Chem.* 267, 16755–16758 (1992).
Shuman, *J. Biol.Chem.* 269, 32678–32684 (1994).
Sikorska and Walker In *When Cells Die.* (eds Lockshin, R. A., Zakeri, Z., and Tilly, J. L.) 211–242 (Willey-Liss, Inc., New York; 1998).
Staley et al., *Cell Death Diff.* 4, 66–75 (1997).
Walker et al., *Annals NY Acad Sci* 887:48–59 (1999).
Widlak P. et al., *J Biol Chem* 275:8226–32 (2000).

We claim:

1. A method of detecting apoptotic cells in a cellular sample, comprising the steps of obtaining a cellular sample; contacting the cellular sample with a solution comprising a nucleic acid molecule and a topoisomerase I enzyme, the nucleic acid molecule being cleavable by the topoisomerase I enzyme and ligatable to a 5'OH; and detecting the nucleic acid molecule ligated to a 5'OH of the DNA of the cellular sample, wherein the detection of the nucleic acid molecule ligated to a 5'OH of the DNA of the cellular sample correlates to the presence of apoptotic cells.

2. The method of claim 1 wherein the cellular sample is a tissue section.

3. The method of claim 1 further comprising the step of fixing the cellular sample.

4. The method of claim 1 wherein the nucleic acid molecule comprises a detectable label.

5. The method of claim 4 wherein the detectable label is selected from the group consisting of enzymes, small molecules, chromophores, fluorophores and radiolabeled materials.

6. The method of claim 4 wherein the detectable label is a fluorophore.

7. The method of claim 4 wherein the detectable label is FITC.

8. The method of claim 1 wherein the detecting is by microscopy.

9. The method of claim 1 wherein the nucleic acid molecule has a recognition site for an endonuclease.

10. The method of claim 1 wherein the topoisomerase I enzyme is vaccinia DNA topoisomerase I.

11. The method of claim 1 wherein the 5' OH is at an overhang.

12. The method of claim 1 wherein the 5' OH is at a recessed end.

13. The method of claim 11 wherein the nucleic acid molecule has a recognition site 2 to 10 nucleotides from the 3' end of the oligonucleotide duplex.

14. The method of claim 1 wherein the 5' OH is at a blunt end.

15. The method of claim 1 wherein the nucleic acid molecule has a topoisomerase I enzyme recognition site and a nick in the opposite strand of DNA.

16. The method of claim 15 wherein the topoisomerase I enzyme recognition site is 5'-CCCTT-3' (SEQ ID NO: 4).

17. The method of claim 15 wherein the nick in the opposite strand of DNA is directly opposite of the point of cleavage at the recognition site.

18. The method of claim 15 wherein cleavage of the nucleic acid molecule by topoisomerase I forms nucleic acid molecule A and nucleic acid molecule B.

19. The method of claim 18 wherein the solution further comprises a nucleic acid ligase enzyme, wherein nucleic acid molecule B is ligatable to a 5'PO$_4$ and detection of nucleic acid molecule A ligated to a 5'OH of the cellular sample and nucleic acid molecule B ligated to a 5'PO$_4$ of the cellular sample correlates to the presence of apoptotic cells.

20. The method of claim 19 wherein the 5' OH is at an overhang.

21. The method of claim 19, wherein the 5' OH is at a recessed end.

22. The method of claim 19 wherein the 5' OH is at a blunt end.

23. The method of claim 19 wherein nucleic acid molecule A and nucleic acid molecule B comprise detectable labels.

24. The method of claim 23 wherein the detectable labels are selected from the group consisting of enzymes, small molecules, chromophores, fluorophores and radiolabeled materials.

25. The method of claim 24 wherein one detectable label is FITC and the other detectable label is rhodamine.

26. The method of claim 19 wherein the nucleic acid ligase enzyme is T4 DNA ligase.

27. A method of detecting apoptotic cells in a cellular sample comprising the steps of: isolating DNA from a cellular sample; contacting the DNA with a solution comprising a nucleic acid molecule and a topoisomerase I enzyme, the nucleic acid molecule being cleavable by the topoisomerase I enzyme and ligatable to a 5'OH; and detecting the nucleic acid molecule ligated to a 5'OH of the DNA, wherein the detection of the nucleic acid molecule ligated to a 5'OH of the DNA correlates to the presence of apoptotic cells.

28. The method of claim 27 wherein the nucleic acid molecule comprises a detectable label.

29. The method of claim 28 wherein the detectable label is selected from the group consisting of enzymes, small molecules, chromophores, fluorophores and radiolabeled materials.

30. The method of claim 28 wherein the detectable label is a fluorophore.

31. The method of claim 28 wherein the detectable label is FITC.

32. The method of claim 27 wherein the detecting is by gel electrophoresis.

33. The method of claim 27 wherein the nucleic acid molecule has a recognition site for an endonuclease.

34. The method of claim 27 wherein the topoisomerase I enzyme is vaccinia DNA topoisomerase I.

35. The method of claim 27 wherein the 5' OH is at an overhang.

36. The method of claim 27 wherein the 5' OH is at a recessed end.

37. The method of claim 35 wherein the nucleic acid molecule has a recognition site 2 to 10 nucleotides from the 3' end of the oligonucleotide duplex.

38. The method of claim 27 wherein the 5' OH is at a blunt end.

39. The method of claim 27 wherein the nucleic acid molecule has a topoisomerase I enzyme recognition site and a nick in the opposite strand of DNA.

40. The method of claim 39 wherein the topoisomerase I enzyme recognition site is 5'-CCCTT-3' (SEQ ID NO: 4).

41. The method of claim 39 wherein the nick in the opposite strand of DNA is directly opposite of the point of cleavage at the recognition site.

42. The method of claim 39 wherein cleavage of the nucleic acid molecule by topoisomerase I forms nucleic acid molecule A and nucleic acid molecule B.

43. The method of claim 42 wherein the solution further comprises a nucleic acid ligase enzyme, wherein nucleic acid molecule B is ligatable to a 5'$PO_4$ and detection of nucleic acid molecule A ligated to a 5'OH of the DNA and nucleic acid molecule B ligated to a 5'$PO_4$ of the DNA correlates to the presence of apoptotic cells.

44. The method of claim 43 wherein the 5' OH is at an overhang.

45. The method of claim 43 wherein the 5' OH is at a recessed end.

46. The method of claim 43 wherein the 5' OH is at a blunt end.

47. The method of claim 43 wherein the nucleic acid molecule A and nucleic acid molecule B comprise detectable labels.

48. The method of claim 47 wherein the detectable labels are selected from the group consisting of enzymes, small molecules, chromophores, fluorophores and radiolabeled materials.

49. The method of claim 48 wherein one detectable label is FITC and the other detectable label is rhodamine.

50. The method of claim 43 wherein the nucleic acid ligase enzyme is T4 DNA ligase.

* * * * *